(12) United States Patent
Myeong et al.

(10) Patent No.: US 7,700,059 B2
(45) Date of Patent: Apr. 20, 2010

(54) METAL OXIDE SOLID SOLUTION AND USE AS OXYGEN STORAGE COMPOSITION AND UV LIGHT SHIELDING AGENT

(75) Inventors: Wan-Jae Myeong, Daejeon (KR); Kyu-Ho Song, Daejeon (KR); Se-Woong Park, Daejeon (KR); Joo-Hyeong Lee, Daejeon (KR); Jin-Soo Baik, Daejeon (KR); Chang-Mo Chung, Daejeon (KR)

(73) Assignee: Hanwha Chemical Corporation, Seoul (KR)

( * ) Notice: Subject to any disclaimer, the term of this patent is extended or adjusted under 35 U.S.C. 154(b) by 1188 days.

(21) Appl. No.: 10/557,939

(22) PCT Filed: May 21, 2004

(86) PCT No.: PCT/KR2004/001221

§ 371 (c)(1),
(2), (4) Date: Nov. 18, 2005

(87) PCT Pub. No.: WO2004/103907

PCT Pub. Date: Dec. 2, 2004

(65) Prior Publication Data

US 2007/0042526 A1    Feb. 22, 2007

(30) Foreign Application Priority Data

May 21, 2003   (KR) ...................... 10-2003-0032357

(51) Int. Cl.
*C01G 1/00* (2006.01)

(52) U.S. Cl. .................................... 423/263; 423/593.1

(58) Field of Classification Search .............. 423/593.1, 423/263; 502/302–304
See application file for complete search history.

(56) References Cited

U.S. PATENT DOCUMENTS

| 5,269,972 | A | | 12/1993 | Arnold, Jr. et al. ........... 252/519 |
| 5,433,878 | A | * | 7/1995 | Arai et al. ................. 252/62.63 |
| 5,453,262 | A | * | 9/1995 | Dawson et al. .............. 501/124 |
| 5,635,154 | A | * | 6/1997 | Arai et al. ................... 423/263 |
| 5,908,800 | A | | 6/1999 | Bonneau et al. ............. 501/103 |
| 5,958,827 | A | * | 9/1999 | Suda et al. .................. 502/304 |
| 6,416,682 | B1 | * | 7/2002 | Krijgsman et al. ....... 252/62.56 |
| 2002/0018741 | A1 | | 2/2002 | Hemme et al. .............. 423/210 |

FOREIGN PATENT DOCUMENTS

| EP | 1055642 | 11/2000 |
| JP | 04055315 | 2/1992 |
| JP | 04284847 | 10/1992 |
| JP | 3341973 | 11/2002 |
| KR | 1003109 | 2/2000 |

* cited by examiner

*Primary Examiner*—Steven Bos
(74) *Attorney, Agent, or Firm*—Abelman, Frayne & Schwab

(57) ABSTRACT

Disclosed is a method for preparing a metal oxide solid solution in nano size. The metal oxide solid solution is prepared by reacting a reactant mixture containing water and at least two water-soluble metal compounds at 200 to 700° C. under a pressure of 180 to 550 bar in a continuous manner, wherein the reactant mixture contains the metal compounds at an amount of 0.01 to 30% by weight in total and the solid solution has a crystallite size of 1 to 1,000 nm. The metal oxide solid solution is, in particular suitable as a UV light shielding agent or as an oxygen storage component.

15 Claims, 1 Drawing Sheet

[Fig. 1]
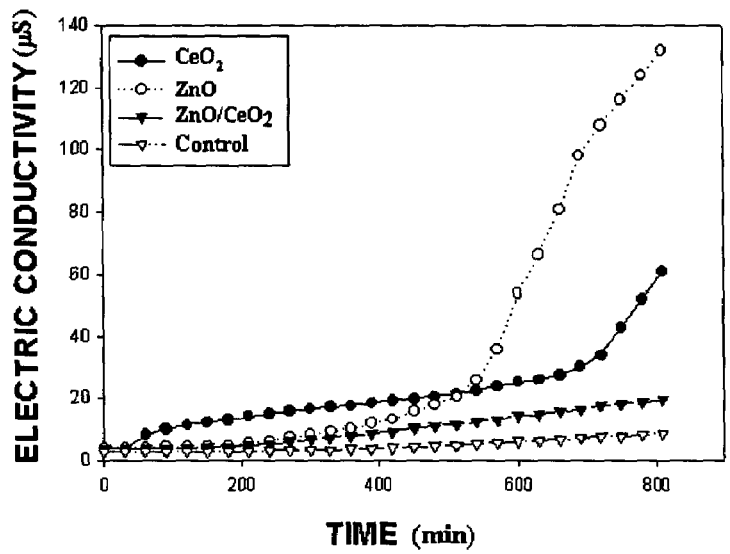
[Fig. 2]
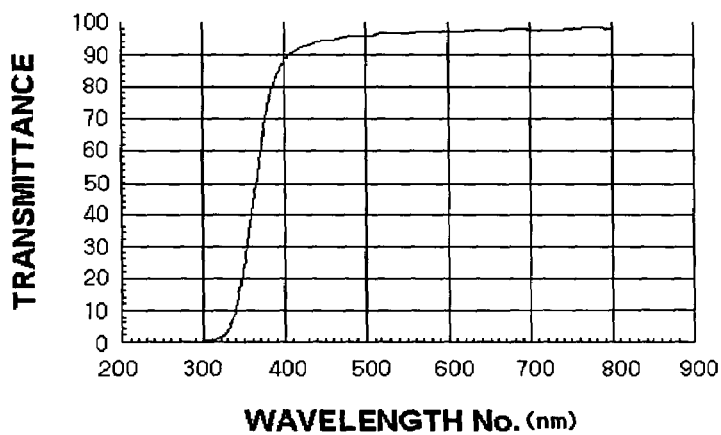
[Fig. 3]
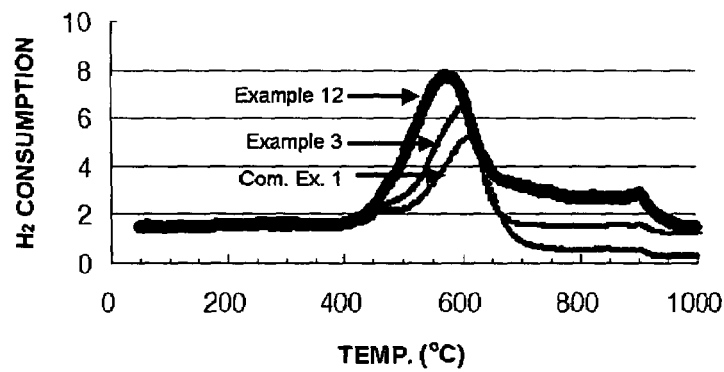

METAL OXIDE SOLID SOLUTION AND USE AS OXYGEN STORAGE COMPOSITION AND UV LIGHT SHIELDING AGENT

TECHNICAL FIELD

The present invention relates to a metal oxide solid solution in nano size. More particularly, the present invention relates to metal oxide solid solutions in nano size, which are superior in UV light shielding effect, lacks catalytic activity, or show only a little increase in crystallite size even after exposure to high temperature with its specific surface area maintained in a high level.

BACKGROUND ART

Formation of solid solutions with metal oxides can open new application fields of metal oxides. That is, metal oxide solid solutions can be applied to a broader range of fields than individual metal oxides can. For example, nano-sized metal oxide solid solutions find applications in various industrial fields, such as UV light shielding, chemical reaction catalysis, optical devices, and so on.

Depending on the phase in which materials are processed, the preparation of metal oxide solid solutions can be classified into vapor, liquid and solid phase processes.

A vapor phase process, exemplified by flame combustion pyrolysis, laser vaporization, plasma vaporization and spray pyrolysis, generally involves the vaporization of metal or metal precursors, which is followed by oxidation.

U.S. Patent Publication No. 2002/018741 A1 discloses the preparation of solid solutions of titania with various metal oxides by use of flame combustion pyrolysis, stating that titania can show improved photocatalytic activity when it forms solid solutions with $Al_2O_3$, $PtO_2$, $MgO$ and/or $ZnO$. The pyrogenic process has advantages of being simple, as in the production of individual metal oxide, and being able to produce fine particles with homogeneity. However, the process suffers from disadvantages of high energy consumption, expensive facilities and low productivity.

Typical of a solid phase process are firing and mechanochemical synthesis. A firing method, which is traditionally used for the preparation of inorganic particles, comprises thermally decomposing precursors for a long period of time at a high temperature in a furnace in the presence of oxygen to produce metal oxides and crystallizing the metal oxides, followed by pulverization to fine particles. The firing method is simple, but has the disadvantage of easily allowing the incorporation of impurities into products and requiring a long period of reaction time at high temperatures.

Nature Materials, Vol. 1, 123-128 (2002) introduces a mechanochemical synthesis method of doping various metals such as $Mg^{2+}$, $Al^{3+}$, $Ti^{4+}$, $Nb^{5+}$ and/or $W^{6+}$ to improve the electric conductivity of $LiFePO_4$, a cathode material of secondary lithium batteries. Such a mechanochemical synthesis method is characterized by a mechanical stimulation (high-speed ball milling) for activating the surface of metal precursor sufficiently to induce reaction thereon. In the process of milling, however, impurities may be incorporated from vials. Additionally, the mechanochemical synthesis requires a long reaction time and a separate calcination process.

As for the liquid phase process, it includes hydrothermal synthesis techniques or sol-gel techniques and the like. U.S. Pat. No. 5,269,972 discloses a method of preparing doped zinc oxide microspheres with resort to a sol-gel technique. This method is able to produce uniform spherical microparticles, but cannot be applied to mass production.

Hydrothermal synthesis techniques, most widely used in the liquid phase process, use water as a reaction medium or a reactant for thermal synthesis. EP 1,055,642 A2 describes the production of metal oxide-doped ceria by use of a hydrothermal synthesis technique. According to this prior art, metal ions as dopants are required to be larger in ion radius or lower in valance than $Ce^{4+}$. Metal ions meeting these requirements include $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, and $Ce^{3+}$. With high UV shielding performance, low catalytic activity, and excellent transparency, the metal oxide-doped ceria may be suitable as UV-light blocking cosmetic materials.

It is reported that ZnO-doped $CeO_2$ exhibits excellent UV-light blocking effects, but low oxidation catalytic activity (Ruxing Li et al., Materials Chemistry and Physics, 75, 39-44 (2002)). Through the hydrothermal synthesis technique, nano-sized particles can be prepared at relatively low temperatures and pressures. The hydrothermal synthesis technique, however, bears formidable disadvantages: expensive oxidant employment, by-product production, and post-processes for treating waste acids. Additionally, a long period of reaction time and the sintering of produced particles are needed for hydrothermal synthesis.

According to wavelength, UV light is subdivided into UV-A and UV-B. Both of these UV radiations are significantly harmful to the skin. For example, the skin turns dark (sun-tan) when excessively exposed to UV-A, and red (sunburn) when to UV-B. Thus, the development of organic or inorganic UV light shielding materials has been directed to protection against both UV-A and UV-B.

Among the organic UV-light shielding materials developed so far, ones with effective UV-A blocking performance are rare. In addition, organic UV-light shielding materials are found to cause skin irritation which is difficult to eliminate. Thus, as such, development research is being focused on inorganic UV light-shielding materials, e.g., titanium dioxide, zinc oxide, etc. However, the inorganic UV-light shielding materials may decompose the organic materials used together therewith, and/or the lipid components on the surface of the skin, because of their catalytic activities. It is thus important to lower the catalytic activities as well as to increase UV-light shielding effects. The smaller in particle size they are, the more effective in UV light shielding ability the inorganic materials are. Further, the inorganic particles of 60 nm or less are transparent as well as showing excellent UV light shielding effects. However, catalytic activities also tend to increase as the size decreases. Accordingly, there is a need for controlling these counter-functional properties.

In this regard, EP 1,055,642 A2 discloses a metal oxide doped ceria which has an excellent UV light shielding effect and transparency, and whose catalytic activity is low. However, much must be done to improve properties of the doped ceria.

Ceria, zirconia and ceria composites have been used in the oxygen storage application. Three-way catalysts for automobile exhausts have excellent conversion efficiency for carbon monoxide (CO), hydrocarbons, and nitrogen oxides (NOx) in a narrow air/fuel ratio range of around 14.6, but the efficiency sharply decreases outside of the range. Due to ready conversion from Ce(III) to Ce(IV) and vice versa, ceria can be used to store oxygen in the fuel lean operation and to release oxygen in the fuel rich operation.

Fuel lean: 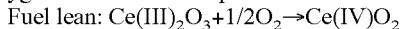
Fuel rich: 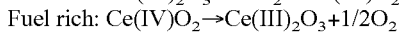

Because of its ability to prevent the problem that the conversion efficiency of three-way catalysts is greatly decreased with even a small change in air/fuel ratio, ceria has been used with three-way catalysts since early 1990s. Three-way catalysts for automobile exhausts are necessarily exposed to high temperatures. In general, the heat resistance of ceria is not high. Accordingly, when exposed to high temperature, ceria undergo the pore filling and the sintering of crystallites, which results in a great loss of surface area, a great increase of crystallite size, and a reduction of oxygen storage capacity and oxygen mobility.

Various attempts have been made to overcame these problems.

As it was found that, when being mixed, especially when forming a solid solution with zirconia, the ceria are improved in thermal resistance as well as in oxygen storage and release capacity, the zirconia-ceria mixed oxides have been applied to three-way catalysts for automobile exhaust. It is also known that the addition of third elements can bring about an improvement in the thermal resistance and oxygen storage capacity of ceria/zirconia composites and that preparation processes and/or compositions have a great effect on the performance of the resulting composites.

Ceria/zirconia composites can be simply prepared by co-precipitation of their precursors and calcinations of co-precipitates at 500-900° C. (Japanese Patent Laid-Open No. Hei. 4-55315). Upon co-precipitation, the solubility of cerium precursors is quite different from that of zirconium precursors according to pH, so that the co-precipitates have non-homogeneous compositions. Further, the solid solution is not formed in the co-precipitation stage, and thus a calcination process should be performed.

Following the impregnation of an aqueous zirconium solution into ceria, the calcination of the impregnant at 700-1, 200° C. produces ceria/zirconia composites (Japanese Patent Laid-Open No. Hei. 4-284847). However, these composites have coarse primary particle sizes and nonhomogeneous compositions.

Both of the above-mentioned processes result in unsatisfactory solid solubilities of about 40% and 20%, respectively, requiring a calcination process at high temperatures and preferably at around 1,600° C. to obtain a sufficient solid solubility of about 100%. However, the solid solutions are not suitable as oxygen storage materials for automobile exhausts because they are large in crystallite size, e.g., 1,000 nm or larger, and small in specific surface area, e.g., 1 $m^2$/g or less.

Korean Patent No. 0313409 discloses a composition based on ceria and zirconia with a cerium/zirconium atom ratio of 1 or higher, optionally added with yttrium, scandium or rare earth metal (elements of atomic Nos 57 to 71) oxides, which have a specific surface area of 35 $m^2$/g or larger after calcination for six hours at 900° C. This composition is prepared by mixing and heating cerium compounds, zirconium compounds and if necessary, yttrium, scandium or rare earth metal compounds in liquid media and calcining the precipitates thus produced. As mentioned above, the calcination, which is conducted to improve the crystallinity of the precipitates, may cause an excessive increase of size of crystallites.

U.S. Pat. No. 5,908,800 describes a process for preparing a mixed cerium and zirconia-based composition, which is of a single cubic phase, comprising the steps of preparing a liquid mixture containing cerium(III) and zirconium, bringing the liquid mixture into contact with carbonate or bicarbonate to form a reactive medium exhibiting a neutral or basic pH during the reaction, collecting precipitates containing cerium carbonate, and calcining the precipitates. After the calcination at 800° C. for six hours, the composition is found to have a specific surface area of 20 $m^2$/g or higher, which remains insufficient for practical application.

Japanese Pat. No. 3341973 discloses a preparation technique of oxide solid solution particles which are improved in oxygen storage capacity and contain crystallites with an average diameter of 100 nm or lower and preferably 12 nm or lower and a specific surface area of 20 $m^2$/g or larger and preferably 50 $m^2$/g or larger by increasing to 70% or higher and preferably to 90% or higher the solid solubility of a mixture containing ceria, zirconia and if necessary, at least one selected from among alkaline earth metal elements and rare earth metal elements except for cerium. The solid solution particles are prepared by a first process of adding surfactant and an alkaline material or hydrogen peroxide to an aqueous solution of cerium compound and zirconium compound to give precipitates and a second process of heating the precipitates at 250° C. to facilitate the dissolution of zirconia to ceria to yield oxide solid solution particles. In Example 19, solid solution particles are described to have a specific surface area of 80 $m^2$/g and an average crystallite diameter of 6 nm The particles, when thermally treated at 300-1,200° C. for five hours, are reduced from 75 $m^2$/g to 5 $m^2$/g in specific surface area and increased from 6 nm to 22 nm in average crystallite diameter. Based on this fact, the particles are believed to still be insufficient in thermal resistance.

DISCLOSURE OF INVENTION

Technical Problem

Leading to the present invention, the intensive and thorough research on the preparation of metal oxide solid solution particles in nano size, conducted by the present inventors with the aim of overcoming economic problems such as long reaction time periods and post-processes for treating by-products, resulted in the finding that the reaction of water with an aqueous metal salt solution containing at least two metal salts under a subcritical or supercritical condition in a continuous manner can allow the preparation of fine particles of metal oxide solid solutions without conducting a sintering process.

Accordingly, it is an object of the present invention to provide a method for preparing a metal oxide solid solution which has an advantage of physical properties over single metal oxides and is economically favorable.

It is another object of the present invention to provide metal oxide solid solutions in nano size, which are superior in UV light shielding effect, lacks catalytic activity, or show only a little increase in crystallite size even after exposure to high temperature with its specific surface area maintained in a high level.

It is a further object of the present invention to provide uses of the metal oxide solid solution.

Technical Solution

In accordance with a first aspect of the present invention, there is provided a method for preparing a metal oxide solid solution, comprising reacting a reactant mixture containing water and at least two water-soluble metal compounds at 200 to 700° C. under a pressure of 180 to 550 bar in a continuous manner, wherein the reactant mixture contains the metal compounds at an amount of 0.01 to 30% by weight in total and the solid solution has a crystallite size of 1 to 1,000 nm. In a preferred version of the first aspect, the reaction mixture is provided by preheating and pre-pressuring the water, separately preparing an aqueous mixed metal solution or a slurry containing the metal compounds, and mixing the preheated and pre-pressurized water with the mixed metal solution or slurry.

In accordance with a second aspect of the present invention, there is provided a method for preparing a metal oxide solid solution, comprising reacting a reactant mixture comprising (i) water, (ii) a water-soluble cerium compound, and (iii) a water-soluble metal compound selected from the group consisting of zinc compounds, yttrium compounds, scandium compounds, compounds of Lanthanides except for cerium, alkaline earth metal compounds and combinations thereof, at 200 to 700° C. under a pressure of 180 to 550 bar in a continuous manner, wherein the reactant mixture contains the metal compounds at an amount of 0.01 to 30% by weight in total and the solid solution has a crystallite size of 1 to 100 nm. In a preferred version of the second aspect, the reactant mixture is provided by preheating and pre-pressuring the water, separately preparing an aqueous mixed metal solution or a slurry containing the water-soluble cerium compound and the water-soluble metal compound, and mixing the preheated and pre-pressurized water with the mixed metal solution or slurry. The metal oxide solid solution prepared above may be applied to the UV-light shielding field.

In accordance with a third aspect of the present invention, there is provided a method for preparing a metal oxide solid solution, comprising reacting a reactant mixture comprising (i) water, (ii) a water-soluble cerium compound, and (iii) a water-soluble zirconium compound at 200 to 700° C. under a pressure of 180 to 550 bar in a continuous manner, wherein the reactant mixture contains the cerium compound and zirconium compound at an amount of 0.01 to 30% by weight in total and the solid solution has a crystallite size of 1 to 10 nm and a specific surface area of at least 100 m$^2$/g. In a preferred version of the third aspect, the reactant mixture is provided by preheating and pre-pressuring the water, separately preparing an aqueous mixed metal solution or a slurry containing the water-soluble cerium compound and the water-soluble zirconium compound, and mixing the preheated and pre-pressurized water with the mixed metal solution or slurry. In another version, the aqueous mixed metal solution further contains at least one water-soluble metal compound selected from scandium compounds, yttrium compounds, compounds of Lanthanide metals except for cerium. The metal oxide solid solution prepared above may be applied to oxygen storage.

Advantageous Effects

Metal oxide solid solution particles in nano size can be prepared, as described hereinafter, in a short time period without conducting a sintering process, by the method of the present invention in which at least two aqueous metal salt solutions are reacted in a continuous manner under a subcritical or supercritical condition.

Also, the metal oxide solid solutions prepared according to the present invention are suitable as UV light shielding agents because they are superior in UV light shielding effect as well as being friendly to the skin due to lack of the catalytic activity. Additionally, the solid solutions can effectively act as oxygen storage components because they show only a little increase in crystallite size upon exposure to high temperature with their specific surface area maintained in a high level. Furthermore, the metal oxide solid solutions which are prepared through a process utilizing subcritical or supercritical water according to the present invention, are in nano size on synthesis while showing high solid solubility and excellent composition homogeneity over the body.

DESCRIPTION OF DRAWINGS

The above and other objects, features and advantages of the present invention will be more clearly understood from the following detailed description taken in conjunction with the accompanying drawings, in which:

FIG. 1 is a graph showing electric conductivities of the zinc oxide-ceria solid solution particles prepared in Example 2, zinc oxide, ceria and a control according to time;

FIG. 2 is a UV-VIS transmittance spectrum of the zinc oxide-ceria solid solution prepared in Example 2; and FIG. 3 is a graph in which TPR of the ceria-zirconia solid solution (prepared in Example 3) and the ceria-zirconia-lanthana solid solution (prepared in Example 12 and Comparative Example 1) was plotted versus temperature.

BEST MODE

According to the first aspect of the present invention, metal oxide solid solutions are prepared by reacting water and a reactant mixture containing at least two water-soluble metal compounds at 200 to 700° C. under a pressure of 180 to 550 bar in a continuous manner.

As for water, deionized water is preferable. Metal compounds, if soluble in water, can be used without specific limitations. Useful is the metal selected among elements of Groups IA, IB, IIA, IIB, IIIA, IIIB, IVA, IVB, VA, VB VIA, VIB, VIIA, VIIB, VIIIB, transition metal Lanthanides comprising Lanthanides and Actinides, and combinations thereof. Specific examples of the metal elements useful in the present invention include Al, Sc, Ga, Li, Mg, Ca, Sr, Ba, Y, Nb, La, Ti, Zr, Cr, Nb, W Mn, Fe, Ru, Rh, Pd, Ir, Pt, Co, Ni, Cu, Ag, Zn, Cd, Ce, Pr, Nd, Sm, Eu and Gd.

In the present invention, the ratio between two or more metals in the solid solutions may vary according to the application fields and usage techniques of metal oxides.

Each of the metal compounds useful in the present invention may be the same or different, and examples of which include hydroxides, chlorides, bromides, iodides, nitrates, sulfonates, carbonates, organic acid salts, and metal complexes with preference to nitrates and iodides in terms of solubility in water, corrosion of facilities, and economic aspects.

In accordance with the present invention, the metal compounds may be used as aqueous solutions or slurries. When account is taken of feasibility and precise amount upon feeding to continuous equipments, aqueous solutions are more preferable. The total weight of two or more metal compounds used is preferably on the order of 0.01 to 30% and preferably on the order of 0.05 to 15% based on the total weight of the reactant mixture. If too little metal compounds are used, the productivity of the process is too low. On the other hand, if too much metal compounds are used, the resulting mixed oxide composition is too viscous to flow in a continuous manner from facilities.

According to the present invention, the continuous reaction is conducted under a subcritical or supercritical condition of 200° C. or higher and 180 bar or higher, preferably at 200 to 700° C. under 180 to 550 bar, and more preferably at 300 to 550° C. under 200 to 400 bar. For example, if the reaction temperature is below 200° C. or the reaction pressure is below 180 bar, large particles of insufficient crystallinity form. On the other hand, excessively high temperatures or pressures make it difficult to provide equipments and materials suitable for use in such conditions.

In a preferred embodiment of the present invention, water (preferably, deionized water) is pre-heated and pre-pressurized in advance, and is continuously mixed with an aqueous mixed metal salt solution or slurry to reach desired reaction temperatures and pressures in a short time period. Pre-pressurization is preferably conducted with a pressure of 180 bar or higher. As for the pre-heating, the temperature is dependent on kinds of metal oxides and preferably is so low as not to cause the hydrolysis of metal salts, such as room temperature. As mentioned above, achieving a desirable reaction condition in a short time period prevents an excessive increase in crystallite size or in crystallite size distribution, which may be caused when temperature and pressure elevation time is extended.

In order to control solid dissolution efficiencies, particle sizes, configurations and physical properties of the solid solutions of metal oxides and to control their preparation rates, an alkaline solution such as ammonia or an acidic solution such as sulfuric acid may be added at an amount of 0.1 to 20 moles per mole of the entire metal compounds before or after the reaction of the present invention. Furthermore, a reductant such as hydrogen or an oxidant such as oxygen or hydrogen peroxide may be added at an amount of 0.1 to 20 moles per mole of the entire metal compounds before or after the reaction.

Where an alkaline or acidic solution and/or a reductant or oxidant is added, not only is the solid solubility of metal oxides improved, but also the resulting particles have small sizes. Also, it is possible to produce metal oxide particles in a desired configuration such as a spherical form, a rectangular form, a plate form and etc, according to the addition amounts and techniques of the alkaline or acidic solution and/or the reductant or oxidant. In addition, the physical properties of the metal oxides can be controlled with solid solubility, particle size and configuration.

As described above, the aqueous metal compound solution or slurry is primarily mixed with an alkaline solution, preferably ammonia water to promote a hydrolysis reaction and secondarily with pre-heated and pre-pressurized water (preferably, deionized water) to achieve a dehydration condition. Hydroxides may be produced by the hydrolysis, and the acidity and temperature of solution according to kinds of the produced metal hydroxides should be appropriately adjusted since their solubilities vary greatly with the acidity and temperature.

In order to apply the fine particles of metal oxide solid solution to specific purposes, the present invention may further comprise the processes of cooling a slurry of the fine particles of metal oxide solid solution, concentrating and isolating the fine particles from the slurry, and drying them. Cooling can be achieved by use of a heat exchanger. For concentration and isolation, centrifugation and/or filtration techniques may be adopted. Specific examples of drying techniques include oven drying, freeze drying, and spray drying. It is possible to conduct isolation and drying simultaneously by spraying at high temperatures and high pressures. A washing process, if necessary, may be further executed.

The fine particles of metal oxide solid solution prepared according to the first aspect of the present invention range, in crystallite size, from 1 to 1,000 nm and more preferably from 1 to 500 nm. For example, when the crystallite size is below 1 nm, the particles are difficult to handle, and an excessive aggregation happens therebetween, causing an increase in the size of primary or secondary particles. On the other hand, when the crystallite size exceeds 1,000 nm, the physical properties of the fine particles are not advantageous.

Crystallite sizes are calculated from the full width at half maximum of (hkl) plane out of XRD peaks, using the Scherrer equation:

$$D_{hkl} = K\lambda/(\beta \cos \theta)$$

In this equation, $D_{hkl}$ is the crystallite size of (hkl) lattice plane, K is the Scherrer constant (0.9 for this case), $\lambda$ is the wavelength of X ray (CuX$\alpha$), $\beta$ is the full width at half maximum (revised value) of a diffraction peak of a sample, and $\theta$ is the incident angle of X ray to (hkl) plane.

In accordance with a second aspect of the present invention, there are provided UV light shielding, skin-friendly metal oxide solid solution particles of nano size which are superior in UV light shielding effect to and have far lower catalytic activity than the conventional metal oxide solutions.

The metal oxide solid solution of the second aspect of the present invention is a ceria solid solution containing a metal oxide selected from the group consisting of zinc oxide, yttrium oxide, scandium oxide, oxides of Lanthanides except for cerium, alkaline earth metal oxides, and combinations thereof, which is prepared by reacting a reactant mixture comprising (i) water, (ii) a water-soluble cerium compound, and (iii) a water-soluble metal compound selected from the group consisting of zinc compounds, yttrium compounds, scandium compounds, compounds of Lanthanides except for cerium, alkaline earth metal compounds and combinations thereof, at 200 to 700° C. under a pressure of 180 to 550 bar in a continuous manner. The total amount of all of the metal compounds used is on the order of 0.01 to 30% and preferably on the order of 0.05 to 15% based on the weight of the reactant mixture. As described above, water (preferably, deionized water) is preferably pre-heated and pre-pressurized in advance of mixing with the aqueous mixed metal solution or slurry, so as to achieve a desired reaction temperature and pressure condition in a short time period. More preferably, the aqueous mixed metal solution or slurry is also pre-pressurized before mixing with the pre-pressurized and pre-heated water.

The water-soluble cerium compounds and other metal compounds used in the second aspect are preferably in salt forms. Salts suitable for cerium and other metals may be the same or different, and their examples include hydroxides, bromides, iodides, nitrates, sulfates, carbonates and organic acid salts with preference to nitrates, carbonates and hydroxides. Except for cerium compounds, zinc, yttrium and calcium compounds are more preferable and may be used alone or in combination.

To improve UV light shielding effects, the mole ratio of the other metal oxide to ceria in the final solid solution product is on the order of 0.01 to 0.6 and preferably on the order of 0.03 to 0.5. Within the range, the amount of cerium compound and other metal compounds in the reactant mixture may be adjusted.

In a preferred embodiment of the second aspect of the present invention, the aqueous mixed metal solution or slurry is mixed with an alkaline solution, preferably ammonia water, to promote a hydrolysis reaction, followed by mixing the resulting mixture with pre-heated and pre-pressurized water (preferably, deionized water), to achieve a dehydration condition. Hydroxides can be produced by the hydrolysis and their solubility varies greatly with the acidity and temperature of the aqueous solution or slurry. Thus, in order to prevent an excessive outflow of the hydroxides due to their dissolution, ammonia water have such a concentration as to maintain the acidity of the resulting solution or slurry at pH 4 or higher and preferably at pH 7 or higher. Additionally, the ammonia-mixed solution or slurry is preferably kept at as low a temperature, e.g., 200° C. or less, so as not to cause a dehydration reaction.

In crystallite size, the metal oxide-ceria solid solution prepared according to the second aspect of the present invention ranges from 1 to 100 nm and preferably from 1 to 60 nm. For example, when the crystallite size exceeds 100 nm, the ceria solid solution cannot exhibit sufficient UV light shielding effects and has a low transparency. On the other hand, when the crystallite size is less than 1 nm, the ceria solid solution particles provide have an unpleasant feel to the skin and are difficult to handle. In particular, the zinc oxide-ceria solid solution particles having a crystallite size of 1 to 100 nm has an excellent UV-shielding effect as well as low catalytic activity. Taking advantage of these properties, the metal oxide-ceria solid solution in nano-size according to the present invention can be used as an effective UV light shielding agent.

In accordance with a third aspect of the present invention, there is provided a ceria-zirconia solid solution of nano size with excellent thermal resistance for oxygen storage, which overcomes the problem of insufficient thermal resistance attributed to the fact that when a conventional three-way catalyst is exposed to high temperatures together with an oxygen storage components, the catalyst is greatly decreased in specific surface area and greatly increased in crystallite size due to the fusion of pores and the sintering of crystalline particles.

The ceria-zirconia solid solution according to the third aspect of the present invention is prepared by reacting a reactant mixture comprising (i) water, (ii) a water-soluble cerium compound, and (iii) a water-soluble zirconium compound at 200 to 700° C. under a pressure of 180 to 550 bar in a continuous manner, wherein the total amount of all of the metal compounds used is on the order of 0.01 to 30% and preferably on the order of 0.05 to 15% of the weight of the reactant mixture. As described above, water (preferably, deionized water) is preferably pre-heated and pre-pressurized before reaction with the aqueous mixed metal compound solution or slurry, so as to achieve a desired reaction temperature and pressure condition in a short time period. More preferably, the aqueous mixed metal compound solution or slurry is also pre-pressurized before mixing with the pre-pressurized and pre-heated water. In particular, the solid solution may be advantageously applied for oxygen storage when the male ratio of zirconia to ceria in the final solid solution ranges from about 0.1 to 0.9. Within the range, the amount of cerium compound and zirconium compounds in the reactant mixture may be adjusted.

If necessary, the reactant mixture may further comprise (iv) at least one metal compound selected from the group consisting of yttrium compounds, scandium compounds, and compounds of Lanthanide metals except for cerium. Preferable is a metal compound selected from the group consisting of yttrium compounds, lanthanum compounds, praseodymium compounds and neodymium compounds. In this case, this metal oxide is preferably present at an amount of 0.001 to 0.2 in the final solid solution on the molar basis.

As for cerium, zirconium, and other metal compounds used in the present invention, they are preferably in salt forms. The salts suitable for cerium, zirconium and the other metals may be the same or different and their examples include hydroxides, bromides, iodides, nitrates, sulfates, carbonates and organic acid salts with preference to nitrates, carbonates and hydroxides. Preferable among Lanthanide metals are lanthanum (La), praseodymium (Pr), neodymium (Nd), and samarium (Sm).

In a preferred embodiment of the third aspect of the present invention, the aqueous mixed metal solution or slurry is mixed with an alkaline solution, preferably ammonia water, to promote a hydrolysis reaction, followed by mixing the resulting mixture with pre-heated and pre-pressurized water (preferably, deionized water) to achieve a de-hydration condition. Hydroxides can be produced by the hydrolysis and their solubility varies greatly with the acidity and temperature of the aqueous solution or slurry. Thus, in order to prevent an excessive outflow of the hydroxides due to their dissolution, ammonia water have such a concentration as to maintain the acidity of the resulting solution or slurry at pH 4 or higher and preferably at pH 7 or higher. Additionally, the ammonia mixed solution is preferably kept at as low a temperature, e.g., 200° C. or less, so as not to cause a dehydration reaction.

The ceria-zirconia solid solution particles prepared according to the third aspect of the present invention preferably range, in crystallite size, from 1 to 10 nm and has a specific surface area of 100 m$^2$/g or greater and preferably 130 m$^2$/g or greater. Because the size of crystals is proportional to that of crystallites, smaller crystallite sizes result in smaller crystal sizes. Accordingly, small crystallite sizes not only allow a large population of oxygen molecules to be present on crystal surfaces but also facilitate the dispersion of the precious metal impregnated as a catalytically active component, thereby improving the oxygen storage capacity. However, when crystallite sizes are too small, aggregation of crystals occurs to increase fusion of micropores upon exposure to high temperatures, resulting in a deteriorated oxygen storage performance. Specific surface areas are measured by nitrogen adsorption according to ASTM D 3663-92 based on the BET (Brunauer-Emmett-Teller) method. Larger specific surface areas are expected to collect a larger proportion of the oxygen molecules on the surface of the composite and to improve the nobility of oxygen, thus contributing to a higher oxygen storage capacity. Additionally, because a larger specific surface area is advantageous to disperse the precious metal elements in pregnated as catalytically active components, a catalyst for automobile exhaust can be produced with superior catalytic activity provided thereon.

When being calcined at 1,000° C. for six hours, the ceria-zirconia solid solution according to the third aspect of the present invention maintain a crystallite size at 20 nm or less and preferably at 15 nm or less and a specific surface area at 20 m$^2$/g or greater or preferably at 30 m$^2$/g or greater. In addition, upon calcination at 900° C. for six hours, the specific surface area is not reduced to 50 m$^2$/g or less.

As a rule, a decrease of specific surface area upon exposure to high temperatures reduces the proportion of the oxygen molecules present on crystal surfaces and causes the burial, sintering or alloying of the impregnated precious metals, thereby greatly deteriorating the oxygen storage capacity and catalytic performance. Accordingly, larger specific surface areas even upon exposure to high temperatures are more preferable.

In particles comprising a mixed ceria-zirconia (binary system) or ceria-zirconia-third metal oxide (ternary system) prepared by a conventional co-precipitation or impregnation method, crystallite sizes may be maintained at 20 nm or less, but the specific surface area is difficult to maintain at 35 m$^2$/g or higher after calcination at 900° C. for six hours and 10 m$^2$/g or higher after calcination at 1,000° C. for six hours.

On the contrary, the ceria-zirconia solid solution of the present invention exhibits very small increases of crystallite size at high temperatures as well as having relatively large specific surface areas even after calcination. It is believed that the particles comprising the ceria-zirconia composition show excellent thermal resistance, which is attributed to the fact that highly crystalline particles of nano-size can be obtained, with a very homogeneous phase of solid solution formed at high solid solubility, by the preparation method of the present invention.

Taking advantage of the excellent thermal properties, the ceria-zirconia solid solutions of the present invention can be applied to various fields including automotive de-pollution catalysts, chemical reaction catalysts, solid electrolytes, electrode materials, ceramic-dispersed reinforcements, UV light shielding agents, oxygen sensors and the like. One of the most promising fields pertains to oxygen storage/release capacity for use in three-way catalysts for automobile exhaust. Three-way catalysts convert carbon monoxide (CO), hydrocarbons, and nitrogen oxides ($NO_x$) into materials of low environmental load or toxicity, such as carbon dioxide and nitrogen, through oxidation or reduction. Typically, a three-way catalyst is prepared by washcoating precious metal, such as Pt, Pd and Rh, alumina and an oxygen storage/release material onto a porous honeycomb.

MODE FOR INVENTION

Example 1

While being pumped at a rate of 80 g per min through a tube having an outer diameter of ¼ inch, deionized water was preheated to 550° C. and pre-pressurized to 250 bar. Separately, while being pumped at a rate of 8 g per min through respective tubes having an outer diameter of ¼ inch, an aqueous mixed metal solution containing 0.99 wt % of yttrium nitrate and 11.0 wt % of zirconium nitrate. While being pumped at a rate of 8 g per min through a tube having an outer diameter of ¼ inch, 36.1 wt % ammonia water was pressurized to 250 bar. The aqueous mixed metal solution containing yttrium nitrate and zirconium nitrate was mixed with the ammonia water in a primary mixer (primary mixing) and then with the preheated and pre-pressurized water under a pressurized condition in a secondary mixer (secondary mixing), followed by reaction at 400° C. for 0.2 sec. The concentration of the metal nitrates was 1.0 wt % in total. The slurry thus produced was cooled and centrifuged to isolate particles.

The particles were found to be zirconia containing yttrium oxide at an amount of 3 mol %, as analyzed by ICP-MS, and to have a spherical form ranging, in diameter, from 3 to 20 nm, as measured by SEM Based on the XRD analysis, in which peaks appeared showing zirconia properties but not yttrium oxide properties, the particles were determined as an yttrium oxide-zirconia solid solution. The particles were found to have a specific surface area of 141 $m^2/g$ as measured by the BET method. The above data demonstrated that even though it was synthesized in a shorter time period (1 sec or less) by the method of the present invention than by conventional methods, the yttrium oxide-zirconia solid solution had highly crystalline properties without conducting a calcination.

Example 2

While being pumped at a rate of 35 g per min through a tube having an outer diameter of ¼ inch, deionized water was preheated to 510° C. and pre-pressurized to 300 bar. Separately, while being pumped at a rate of 4 g per min through a tube having an outer diameter of ¼ inch, an aqueous mixed metal solution containing 8.97 wt % of cerium nitrate and 1.54 wt % of zinc nitrate was pressurized to 300 bar. Apart from the aqueous mixed metal solution, while being pumped at a rate of 3 g per min through a tube having an outer diameter of ¼ inch, 6.43 wt % ammonia water was pressurized to 300 bar. Under a pressurized condition, the aqueous solution containing cerium nitrate and zinc nitrate, the ammonia water, and the pre-heated and pre-pressurized deionized water were mixed in a mixer, followed by reaction for 0.8 sec at 385° C. The concentration of the metal nitrates was 1.0 wt % in total. The slurry thus produced was cooled and centrifuged to isolate particles.

The particles were found to be ceria containing zinc oxide at an amount of 20 mol %, as analyzed by ICP-MS and to have an octahedral form ranging, in size, from 10 to 40 nm, as measured by SEM. Based on the XRD analysis that peaks appeared showing ceria properties but lacking zinc oxide properties, the particles were recognized as a zinc oxide-ceria solid solution. Calculation using the Scherrer equation from the full width at half maximum of XRD peaks showed a crystallite size of 10.3 nm The particles were found to have a specific surface area of 90 $m^2/g$ as measured by the BET method.

Through a mixture of 1 g of the zinc oxide-ceria solid solution and 10 g of castor oil, air was penetrated at a speed of 416 ml/min at 120° C., and the air emitted from the mixture was passed through deionized water, which was then measured for electroconductivity.

As seen in FIG. 1, zinc oxide-ceria solid solution particles underwent a significant reduction of catalytic oxidation activity. The ceria and the zinc oxide employed as comparative materials in FIG. 1 were respectively prepared from nitrates of single metal elements in a method similar to that of Example 1. According to SEM analysis, it was found that the ceria was octahedral with a size of 20-80 nm and the zinc oxide was spherical with a size of 50-200 nm 2 g of the zinc oxide-ceria solid solution was mixed with 4 g of methyl cellulose, 10 g of ethyl acetate and 9 g of butyl acetate and then, with zirconia balls (diameter 2.7 mm) for 48 hours in a paint shaker. The resulting mixture was thinly coated on one surface of a UV test tube which was then measured for UV transmittance. As seen in FIG. 2, the transmittance was reduced in the UV A/B region (400 to 290 nm), demonstrating that the zinc oxide-ceria solid solution has an excellent UV light shielding effect.

The above data exhibited that even though being synthesized in a shorter time period (1 sec or less) by the method of the present invention than by conventional methods, the zinc oxide-ceria solid solution of 100 nm or less size is superior in UV light shielding ability and affinity for the skin.

Example 3

While being pumped at a rate of 80 g per min through a tube having an outer diameter of ¼ inch, deionized water was preheated to 550° C. and pre-pressurized to 250 bar. Separately, while being pumped at a rate of 8 g per min through respective tubes having an outer diameter of ¼ inch, an aqueous mixed metal solution containing 13.95 wt % of zirconium nitrate and 4.05 wt % of cerium nitrate was pressurized to 250 bar. While being pumped at a rate of 8 g per min through a tube having an outer diameter of ¼ inch, 18 wt % ammonia water were pressurized to 250 bar. Under a pressurized condition, the aqueous solution containing zirconium nitrate and cerium nitrate, the ammonia water, and the pre-heated and pre-pressurized deionized water were mixed in a mixer, followed by reaction for 0.2 sec at 380° C. The slurry thus produced was cooled and used to isolate particles therefrom. These particles were dried at 100° C. in an oven, followed by calcination for six hours in furnaces of 900° C. and 1,000° C. The particles before and after calcination at 900° C. and 1,000° C. were found to have specific surface areas of 175, 51 and 33 $m^2/g$, respectively, as measured by the BET method, and to have crystallite sizes of 5.1, 8.1 and 9.9 nm, respectively, as calculated from the full length at half maximum of XRD by the Scherrer equation.

Example 4

While being pumped at a rate of 80 g per min through a tube having an outer diameter of ¼ inch, deionized water was preheated to 550° C. and pre-pressurized to 250 bar. Separately, while being pumped at a rate of 8 g per min through respective tubes having an outer diameter of ¼ inch, an aqueous mixed metal solution containing 1.575 wt % of zirconium nitrate and 16.425 wt % of cerium nitrate was pressurized to 250 bar. While being pumped at a rate of 8 g per min through a tube having an outer diameter of ¼ inch, and 10.8 wt % ammonia water were pressurized to 250 bar. Under a pressurized condition, the aqueous solution containing zirconium nitrate and cerium nitrate, the ammonia water, and the preheated and pre-pressurized deionized water were mixed in a mixer, followed by reaction for 0.2 sec at 400° C. The slurry thus produced was cooled and used to isolate particles therefrom. These particles were dried at 100° C. in an oven, followed by calcination for six hours in furnaces of 900° C. and 1,000° C. The particles before and after calcination at 900° C. and 1,000° C. were found to have specific surface areas of 170, 48 and 30 $m^2/g$, respectively, as measured by the BET method, and to have crystallite sizes of 4.8, 7.9 and 9.3 nm, respectively, as calculated from the full length at half maximum of XRD by the Scherrer equation.

Examples 5 to 12

While being pumped at a rate of 96 g per min through a tube having an outer diameter of ¼ inch, deionized water was preheated to predetermined temperatures and pre-pressurized to predetermined pressures. Separately, while being pumped at a rate of 8 g per min through respective tubes having an outer diameter of ¼ inch, an aqueous mixed metal solution containing 7.35 wt % of zirconium nitrate, 11.96 wt % of cerium nitrate and 1.67 wt % of lanthanum nitrate was pressurized to predetermined pressures. While being pumped at a rate of 8 g per min through a tube having an outer diameter of ¼ inch, 4.32 wt % ammonia water was pressurized to predetermined pressures. Under a pressurized condition, the aqueous solution containing zirconium nitrate, cerium nitrate and lanthanum nitrate was mixed with the ammonia water at predetermined temperatures in a primary mixer (primary mixing) and then with the deionized water at predetermined temperatures under predetermined pressure in a secondary mixer (secondary mixing) followed by reaction for 0.2 sec. The slurry thus produced was cooled and used to isolate particles therefrom. These particles were dried at 110° C. for 12 hours or more in an oven, followed by calcination for six hours in furnaces of 900° C. and 1,000° C. The particles before and after calcination at 900° C. and 1,000° C. were calculated for crystallite size from the full length at half maximum of XRD by the Scherrer equation. The results are given in Table 1, below.

It is apparent from Table 1 that the crystallite size ranging from 5 to 7 nm on synthesis remains almost unchanged (6-8 nm) even after calcination at 1,000° C. for six hours. Also, the specific surface area (130 $m^2/g$ or larger on synthesis) was maintained at suitable levels (50 and 30 $m^2/g$) after calcination at 900° C. and 1,000° C. for six hours, respectively.

Comparative Example 1

A composition containing ceria, zirconia and lanthana (molar ratio: $CeO_2:ZrO_2:La_2O_3$=0.4825:0.4825:0.035 as in Examples 5 to 12) was prepared by a conventional co-precipitation process. An aqueous cerium nitrate solution, an aqueous zirconium nitrate solution, and an aqueous lanthanum nitrate solution were mixed in such a stoichiometric amount as to achieve the role ratio. Using oxides of the metal elements, the concentration of the resulting solution was adjusted to 172 g/l. This mixed solution was slowly added to an aqueous solution containing ammonia water hydrogen peroxide. The concentration of ammonia was adjust to 1.7 times larger than that of the nitrate ions contained in the solution of the metal nitrates while hydrogen peroxide to half of that of the metal ions contained in the solution of the metal salts. The precipitates thus formed were filtered, washed and dried at 300° C. At 900° C. and 1000° C., the dried particles were calcined for six hours. The samples dried at 300° C. and calcined at 900° C. and 1,000° C. were found to have crystallite sizes of 6 nm, 20 nm and 32 nm, respectively, as calculated from the full length at half maximum of XRD and to have specific surface areas of 50, 10 and 2 $m^2/g$, respectively, as measured by the BET method.

[Evaluation for Oxygen Storage/Release Capacity]

A TPR (temperature programmed reduction) test was conducted to evaluate the samples of Examples 3 and 12 calcined for six hours at 1,000° C. for oxygen storage/release capacity. The samples were put in quart vials of a TPR reactor. While being introduced into the reactor, air was maintained at 500° C. for one hour and slowly cooled to room temperature. Then, air was substituted with helium gas. Thereafter, while a mixed gas of hydrogen and argon was introduced, instead of helium, with the temperature elevation at a rate of 10° C. per min, the hydrogen consumption attributed to the reduction of oxygen was recorded with a TCD (thermal conductivity detector). After being maintained at 900° C. for 30 min, the temperature was slowly cooled. In FIG. 3, hydrogen consumption amounts are plotted in arbitrary units versus temperatures. In FIG. 3, the larger the area under the graph is, the larger the hydrogen consumption is. Consequently, the data of FIG. 3

TABLE 1

| Exmp. Nos. | Synthesis Condition | | | XRD Crystallite Size (nm) | | Specific Surface Area ($m^2/g$) | | |
|---|---|---|---|---|---|---|---|---|
| | 1' Mixing Temp. (° C.) | 2' Mixing Temp. (° C.) | Press. (bar) | On Synthesis | After 1000° C. calcin. | On Synthesis | After 900° C. calcin. | After 1000° C. calcin. |
| 5 | 25 | 385 | 230 | 6.7 | 6.8 | 149.1 | 56.5 | 34.9 |
| 6 | 25 | 425 | 230 | 5.7 | 6.6 | 143.1 | 60.9 | 39.6 |
| 7 | 25 | 385 | 300 | 5.6 | 7.8 | 144.8 | 54.3 | 36.6 |
| 8 | 25 | 425 | 300 | 5.4 | 7.6 | 133.5 | 59.2 | 38.7 |
| 9 | 80 | 425 | 300 | 5.4 | 6.9 | 134.2 | 54.9 | 34.7 |
| 10 | 80 | 385 | 300 | 5.7 | 7.2 | 141.6 | 51.4 | 32.5 |
| 11 | 80 | 425 | 230 | 5.9 | 6.1 | 142.4 | 53.5 | 34.3 |
| 12 | 80 | 385 | 230 | 6.3 | 6.4 | 151.9 | 50.8 | 32.9 | demonstrates that the ceria-zirconia solid solution and the ceria-zirconia-lanthanum oxide solid solution are superior in oxygen storage capacity.

Examples 13 to 16

The procedure of Examples 5 to 12 was carried out, with the exception that metal nitrates of Table 2, instead of lanthanum nitrate, 25° C. for the primary mixing temperature, 400° C. for the secondary mixing temperature, and 250 bar for the pressure were employed. The concentrations of the metal nitrates were controlled to obtain the same molar ratio as in the composition of Examples 5 to 12. Kinds of metal compounds and properties of the products are given in Table 2, below.

It is apparent from Table 2 that the crystallite sizes (below 10 nm) on synthesis are almost unchanged even after calcination at 1,000° C. for six hours. Also, the specific surface area (130 m$^2$/g or larger on synthesis) was maintained at suitable levels (50 and 30 m$^2$/g) after calcination at 900° C. and 1,000° C. for six hours, respectively.

TABLE 2

| | | Physical Properties of Products | | | | |
|---|---|---|---|---|---|---|
| | | XRD Crystallite Size (nm) | | Specific Surface Area (m$^2$/g) | | |
| Exmp. Nos. | Metal Cpd. | On Synthesis | After 1000° C. Calcin. | On Synthesis | After 900° C. Calcin. | After 1000° C. Calcin. |
| 13 | Y nitrate | 5.7 | 6.8 | 143.5 | 53.3 | 30.6 |
| 14 | Pr nitrate | 5.9 | 6.6 | 140.1 | 56.1 | 36.1 |
| 15 | Nd nitrate | 6.6 | 7.8 | 139.8 | 53.3 | 33.0 |
| 16 | Sm nitrate | 6.2 | 7.0 | 145.3 | 55.6 | 30.1 |

Example 17

A mixture of yttrium nitrate and lanthanum nitrate was used instead of the lanthanum nitrate of Examples 5 to 12. The concentration of each of the nitrates was so adjusted that the mole amount of each metal in the product was half of the lanthanum mole amount of Examples 5 to 12, that is, Y$_2$O$_3$=La$_2$O$_3$=0.0175. The remaining condition was the same as in Examples 13 to 16. Physical properties of the product are given in Table 3, below.

It is apparent from Table 3 that the crystallite size (below 10 nm) on synthesis was retained even after calcination at 1,000° C. for six hours. Also, the specific surface area (130 m$^2$/g or larger on synthesis) was maintained at suitable levels (50 and 30 m$^2$/g) after calcination at 900° C. and 1,000° C. for six hours, respectively.

INDUSTRIAL APPLICABILITY

Metal oxide solid solution particles in nano size can be prepared, as described hereinbefore, in a short time period without conducting a sintering process, by the method of the present invention in which at least two aqueous metal salt solutions are reacted in a continuous manner under a subcritical or supercritical condition.

Also, the metal oxide solid solutions prepared according to the present invention are suitable as UV light shielding agents because they are superior in UV light shielding effect as well as being friendly to the skin due to lack of the catalytic activity. Additionally, the solid solutions can effectively act as oxygen storage components because they show only a little increase in crystallite size upon exposure to high temperature with their specific surface area maintained in a high level. Furthermore, the metal oxide solid solutions which are prepared through a process utilizing subcritical or supercritical water according to the present invention, are in nano size on synthesis while showing high solid solubility and excellent composition homogeneity over the body.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A method for preparing a metal oxide solid solution, comprising reacting a reactant mixture comprising i) water, ii) a water-soluble cerium compound, and iii) a water-soluble metal compound selected from the group consisting of zinc compounds, yttrium compounds, scandium compounds, compounds of lanthanides except for cerium, alkaline earth metal compounds and combinations thereof, at 200 to 700° C. under a pressure of 180 to 550 bar in a continuous manner, wherein the reactant mixture contains the metal compounds

TABLE 3

| | | Physical Properties of Products | | | | |
|---|---|---|---|---|---|---|
| | | XRD Crystallite Size (nm) | | Specific Surface Area (m$^2$/g) | | |
| Exmp. Nos. | Metal Cpd. | On Synthesis | After 1000° C. Calcin. | On Synthesis | After 900° C. Calcin. | After 1000° C. Calcin. |
| 17 | Y nitrate/ La nitrate | 5.6 | 6.2 | 133.7 | 61.5 | 42.4 | at an amount of 0.01 to 30% by weight in total and the solid solution has a crystallite size of 1 to 100 nm.

2. The method as set forth in claim 1 wherein said water-soluble metal compound is in the form of hydroxide, chloride, bromide, iodide, nitrate, sulfate, carbonate, organic acid salts or metal complexes.

3. The method as set forth in claim 1, wherein an alkaline or acidic solution is added at an amount of 0.1 to 20 moles per mole of the total metal compounds, before or during the reaction.

4. The method as set forth in claim 1, wherein a reductant or an oxidant is added at an amount of 0.1 to 20 moles per mole of the total metal compounds, before or during the reaction.

5. The method as set forth in claim 3, wherein the alkaline solution is ammonia water.

6. The method as set forth in claim 1, wherein said reactant mixture is provided by preheating and pre-pressuring i) the water; separately preparing an aqueous mixed metal solution or a slurry containing ii) the water-soluble cerium compound and iii) the water-soluble metal compound; and mixing the preheated and pre-pressurized water with the mixed metal solution or slurry.

7. A method for preparing a metal oxide solid solution, comprising reacting a reactant mixture comprising i) water, ii) a water-soluble cerium compound, and iii) a water-soluble zirconium compound at 200 to 700° C. under a pressure of 180 to 550 bar in a continuous manner, wherein the reactant mixture contains the cerium compound and zirconium compound at an amount of 0.01 to 1% by weight in total and the solid solution has a crystallite size of 1 to 10 nm and a specific surface area of at least 100 m2/g.

8. The method as set forth in claim 7, wherein said reactant mixture is provided by preheating and pre-pressuring i) the water; preparing an aqueous mixed metal solution or a slurry containing ii) the water-soluble cerium compound and iii) the water-soluble zirconium compound; and mixing the pre-heated and pre-pressurized water with the mixed metal solution or slurry.

9. The method as set forth in claim 7, wherein the reactant mixture further comprises iv) at least one water-soluble metal compound selected from the group consisting of scandium compounds, yttrium compounds, and compounds of lanthanide metals except for cerium.

10. The method as set forth in claim 9, wherein the metal oxide from iv) the water-soluble metal compound is present at an amount of 0.001 to 0.2 in the metal oxide solid solution on the molar basis.

11. The method as set forth in claim 7, wherein said metal oxide solid solution has a crystallite size of 20 nm or less and a specific surface area of at least 20 m2/g after being calcined for six hours at 1,000° C. in air.

12. The method as set forth in claim 7, wherein said water-soluble metal compound is in the form of a hydroxide, chloride, bromide, iodide, nitrate, sulfate, carbonate, organic acid salts or metal complexes.

13. The method as set forth in claim 7, wherein an alkaline or acidic solution is added at an amount of 0.1 to 20 moles per mole of the total metal compounds, before or during the reaction.

14. The method as set forth in claim 7, wherein a reductant or an oxidant is added at an amount of 0.1 to 20 moles per mole of the total metal compounds, before or during the reaction.

15. The method as set forth in claim 13, wherein the alkaline solution is ammonia water.

* * * * *